United States Patent
Sisco et al.

(10) Patent No.: US 11,135,401 B2
(45) Date of Patent: Oct. 5, 2021

(54) URINARY CATHETER SUPPORT

(71) Applicant: Regents of the University of Minnesota, Minneapolis, MN (US)

(72) Inventors: Shawn Michele Sisco, Robbinsdale, MN (US); Anthony Itambo, Minneapolis, MN (US); Bita Rajablou, Minneapolis, MN (US); Austin Andrews, Minneapolis, MN (US); Andrew Wloch, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 502 days.

(21) Appl. No.: 15/973,689

(22) Filed: May 8, 2018

(65) Prior Publication Data

US 2018/0326184 A1 Nov. 15, 2018

Related U.S. Application Data

(60) Provisional application No. 62/503,712, filed on May 9, 2017.

(51) Int. Cl.
*A61M 25/02* (2006.01)
*A61M 25/00* (2006.01)

(52) U.S. Cl.
CPC ......... *A61M 25/02* (2013.01); *A61M 25/0017* (2013.01); *A61M 2025/0206* (2013.01);
(Continued)

(58) Field of Classification Search
CPC .............. A61M 25/02; A61M 25/0017; A61M 2025/0206; A61M 2025/0213;
(Continued)

(56) References Cited

U.S. PATENT DOCUMENTS 4,419,097 A * 12/1983 Rowland ................. A61F 5/453
604/174
4,784,647 A * 11/1988 Gross ...................... A61F 5/441
128/DIG. 26

(Continued)

OTHER PUBLICATIONS

Wilde, M. H., McDonald, M. V., Brasch, J., McMahon, J. M., Fairbanks, E., Shah, S., . . . & Scheid, E. (2013). Long-term urinary catheter users self-care practices and problems. Journal of clinical nursing, 22(3-4), 356-367.

(Continued)

*Primary Examiner* — Adam Marcetich
(74) *Attorney, Agent, or Firm* — Brian D. Kaul; Westman, Champlin & Koehler, P.A.

(57) ABSTRACT

A urinary catheter support configured to support an indwelling urinary catheter such that the urinary catheter is secured relative to the penis of a male patient includes a flexible main body having an interior size and configured to receive and accommodate the penis of the male patient. A catheter support is located at a front end of the main body and is configured to support a catheter adjacent a longitudinal axis of the main body. A slot extends along the longitudinal axis through the main body and the catheter support. A strap includes first and second end segments and a middle segment between the first and second end segments. The first and second end segments respectively extend through first and second openings in the main body, and the middle segment extends through an interior of the main body.

20 Claims, 12 Drawing Sheets

(52) U.S. Cl.
CPC ............... *A61M 2025/0213* (2013.01); *A61M 2025/0253* (2013.01); *A61M 2205/584* (2013.01); *A61M 2210/167* (2013.01)

(58) Field of Classification Search
CPC .... A61M 2025/0253; A61M 2205/584; A61M 2210/167; A61F 2002/0072; A61F 5/449; A61F 5/453
See application file for complete search history.

(56) References Cited

U.S. PATENT DOCUMENTS

| | | | |
|---|---|---|---|
| 4,810,247 A | | 3/1989 | Glassman |
| 4,957,487 A | | 9/1990 | Gerow |
| 5,009,649 A | * | 4/1991 | Goulter ................... A61F 5/453 |
| | | | 604/349 |
| 5,087,252 A | | 2/1992 | Denard |
| 5,100,396 A | * | 3/1992 | Zamierowski .... A61F 13/00068 |
| | | | 604/174 |
| 5,263,939 A | * | 11/1993 | Wortrich ................ A61B 17/34 |
| | | | 128/DIG. 26 |
| 5,593,389 A | * | 1/1997 | Chang ................... A61F 5/4408 |
| | | | 604/174 |
| 5,795,334 A | * | 8/1998 | Cochrane, III ....... A61M 25/02 |
| | | | 604/174 |
| 5,980,507 A | * | 11/1999 | Fassuliotis ............ A61F 5/4401 |
| | | | 604/351 |
| 7,803,144 B1 | | 9/2010 | Vollrath |
| 7,959,611 B2 | | 6/2011 | Harvey et al. |
| 8,500,719 B1 | * | 8/2013 | Simpson, Jr. ......... A61M 25/02 |
| | | | 604/544 |
| 8,834,422 B2 | * | 9/2014 | Walker .............. A61M 25/0618 |
| | | | 604/164.01 |
| 2004/0176746 A1 | * | 9/2004 | Forral ..................... A61F 5/453 |
| | | | 604/544 |
| 2005/0101923 A1 | * | 5/2005 | Elson ..................... A61F 5/453 |
| | | | 604/349 |
| 2010/0145314 A1 | * | 6/2010 | Hazan ................... A61M 25/02 |
| | | | 604/544 |
| 2015/0208745 A1 | * | 7/2015 | Duhatschek ........... A41D 13/04 |
| | | | 2/463 |
| 2015/0320576 A1 | * | 11/2015 | Riedel ....................... A61F 2/78 |
| | | | 623/32 |
| 2017/0333244 A1 | * | 11/2017 | Laniado ................. A61F 5/443 |

OTHER PUBLICATIONS

Bell, M. A. (2010). Severe indwelling urinary catheter-associated urethral erosion in four elderly men. Ostomy/wound management, 56(12), 36-39.

Newman, D. K., Willson, M. M. (2011). Review of Intermittent Catheterization and Current Best Practices. Society of Urologic Nurses and Associates Urologic Nursing, pp. 12-29, 48, vol. 31, No. 1.

* cited by examiner

URINARY CATHETER SUPPORT

CROSS-REFERENCE TO RELATED APPLICATION

The present application is based on and claims the benefit of U.S. provisional patent application Ser. No. 62/503,712, filed May 9, 2017, the content of which is hereby incorporated by reference in its entirety.

FIELD

The present invention relates generally to urinary catheters, and more particularly, to a urinary catheter support which is configured to support an indwelling urinary catheter such that the catheter is secured relative to a supporting body part.

BACKGROUND

Some bodily wastes, such as salt, urea and uric acid, are removed from the bloodstream through the filtrating function of the kidneys via the urethra. In some medical conditions, however, such body wastes cannot be eliminated from the body. For example, blockage to the flow of urine may develop in the urethra, or the urine-expelling functions of the bladder may be compromised. Consequently, accumulation of urine in the bladder may result, potentially causing kidney failure or sepsis.

One of the medical interventions which is commonly used to address medical conditions in which urine is not excreted from the bladder includes placement of a urinary catheter in the urethra. Such a urinary catheter, commonly referred to as indwelling catheter, facilitates drainage of urine from the bladder. An indwelling urinary catheter typically includes a hollow, flexible tube which is inserted through the urethra to the bladder of the patient. The discharge end of the tube remains outside the body and is connected to a bag or other container into which the urine is collected. An indwelling urinary catheter may remain in place in a patient's urinary tract for extended periods of time.

One of the limitations of conventional indwelling urinary catheters is that the catheter may be subjected to inadvertent drag from the weight of the urine collection bag into which the urine is discharged. In males, urethral tearing may be caused by transverse pull of an indwelling urinary catheter due to urine bag drag weight or patient movement. Left unchecked, urethral tearing may require a recovery protocol of a second surgery to install a supra-pubic catheter or surgical reconstruction of the urethra, or may otherwise cause permanent bladder dysfunction, require personal assisted care, and negatively impact quality of life.

Past solutions to confining a urinary catheter in the urinary tract of a patient include tethering the catheter to the leg of the patient by using leg bands or adhesive patches. These bands or patches help guide the catheter through clothing and additionally support some weight of the urine collection bag and lessen torsion in the catheter tube. However, when the catheter tube is tethered laterally to the leg of the patient, movement of the patient's body and the catheter may create an abrasive "sawing effect" on the suspended penis, causing erosion which may be severe enough to tear the soft tissue inside the penis, through to the glans or up the penile shaft.

Accordingly, there is an established need for a urinary catheter support which is configured to support an indwelling urinary catheter such that the catheter is secured relative to a supporting body part.

SUMMARY

Embodiments of the present disclosure are directed toward a urinary catheter support that is configured to support an indwelling urinary catheter such that the urinary catheter is secured relative to the penis of a male patient. In some embodiments, the urinary catheter support includes a flexible main body having an interior size and configured to receive and accommodate the penis of the male patient. A catheter support is located at a front end of the main body and is configured to support a catheter adjacent a longitudinal axis of the main body. A slot extends along the longitudinal axis through the main body and the catheter support. A strap includes first and second end segments and a middle segment between the first and second end segments. The first and second end segments respectively extend through first and second openings in the main body, and the middle segment extends through an interior of the main body.

Another embodiment of the urinary catheter support includes a flexible main body having an interior size that is configured to receive and accommodate the penis of a male patient. A catheter support located at a front end of the main body is configured to support a catheter adjacent a longitudinal axis of the main body. A slot extends along the longitudinal axis through the main body and the catheter support. A bushing is received within the catheter support. The bushing includes a bore through which the catheter extends.

Additional embodiments of the present disclosure are directed to a method of supporting a catheter received in the penis of a male patient. In the method, a urinary catheter support is attached to the penis including receiving the penis within an interior of a flexible main body. A bushing is installed within a catheter support at a front end of the main body. The catheter extends through the bushing.

In some embodiments, the attachment of the urinary catheter support to the penis includes extending a strap through a first opening in the main body, between the penis and a sidewall of the main body, and through a second opening in the main body. The strap is then wrapped around the penis and the main body to attach the urinary catheter support to the penis.

In some embodiments of the method, sliding movement of the bushing along the longitudinal axis relative to the catheter support is restricted using one or more various techniques. In one technique, a proximal end of the bushing includes a flange, which is used to restrict sliding movement of a bushing along the longitudinal axis relative to the catheter support. In another technique, a detent is formed in an interior surface of the catheter support and a protrusion is formed on an exterior surface of the bushing. The protrusion is received within the detent to restrict sliding movement of the bushing along the longitudinal axis relative to the catheter support. In yet another technique, a protrusion is formed on the interior surface of the catheter support and a detent is formed on the exterior surface of the bushing. The protrusion is received within the detent to restrict sliding movement of the bushing along the longitudinal axis relative to the catheter support.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
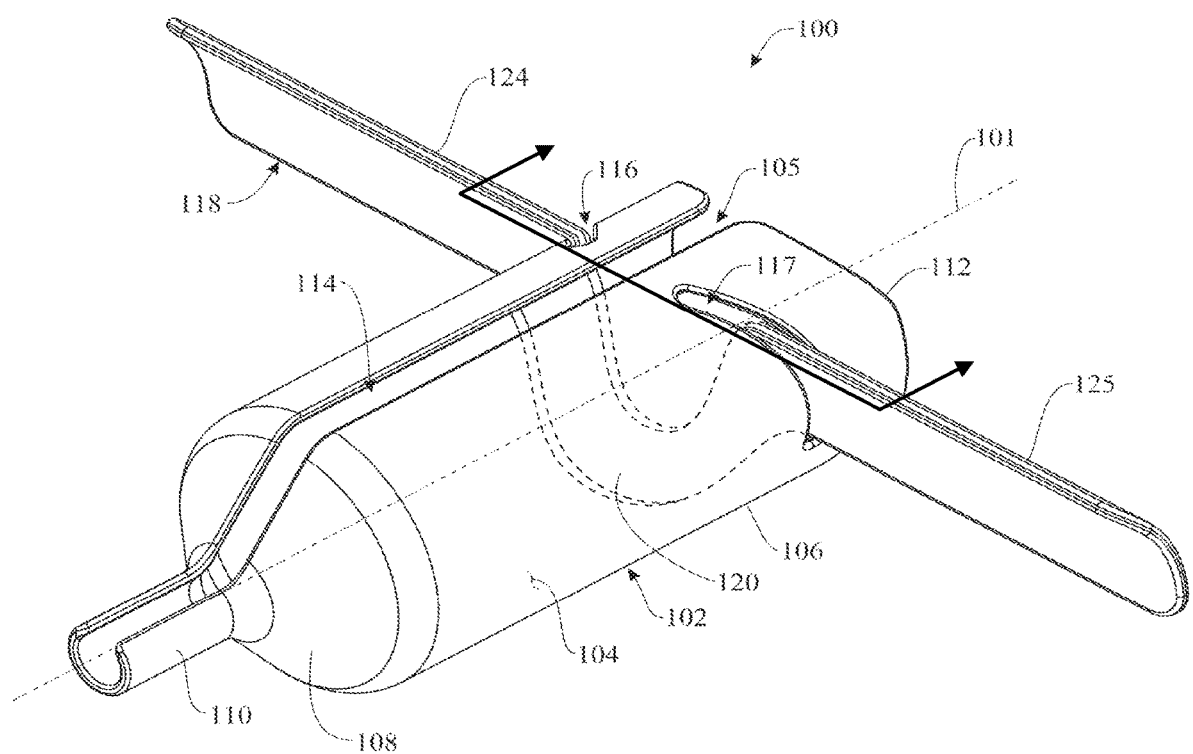
FIG. 1 is a top front perspective view of an exemplary embodiment of a urinary catheter support in accordance with the present disclosure.

Embodiments of the present disclosure are described more fully hereinafter with reference to the accompanying drawings. Elements that are identified using the same or similar reference characters refer to the same or similar elements. The various embodiments of the present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art.

Embodiments of the present disclosure are directed toward a urinary catheter support that is configured to support an indwelling urinary catheter such that the urinary catheter is secured relative to a supporting body part, such as the penis of a male patient. The urinary catheter support centers, stabilizes and supports the catheter, minimizes or eliminates torsion in the catheter tube and protects the urethra, glans and penis during patient mobility, thus preventing penile erosion caused by movement of the catheter and providing the patient comfort, peace of mind and greater freedom of movement.

The illustrations of FIGS. 1-10 show a urinary catheter support 100 in accordance with an illustrative embodiment of the invention. Referring initially to FIG. 1, the urinary catheter support 100 includes a main body 102 which extends along a front-to-back, longitudinal axis 101. The main body 102 has a sidewall 104 which defines a sheath portion 106 of the main body 102. The sheath portion 106 may be generally elongated and cylindrical in shape in substantially concentric alignment with the longitudinal axis 101. An interior 105 of the main body may be partially enclosed and defined by the sidewall 104 of the sheath portion 106. As illustrated in FIGS. 4-9, the main body interior 105 of the sheath portion 106 may be suitably sized and configured to accommodate the penis 128 of a male patient, as will be hereinafter further described.

Figure 2:
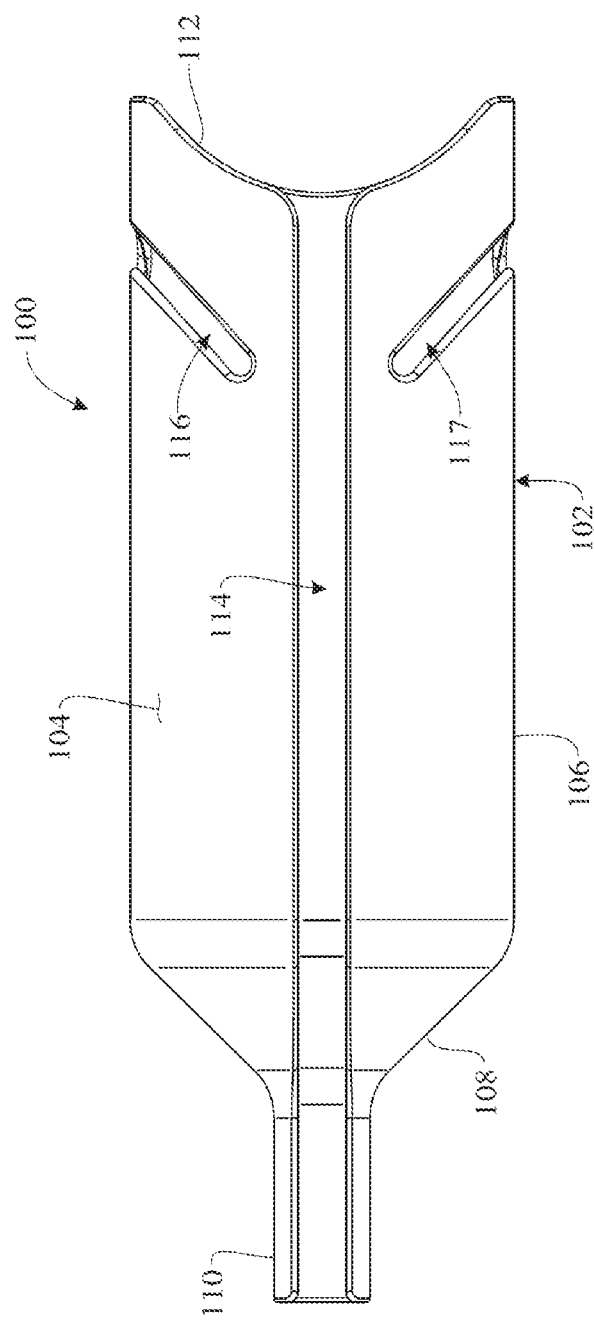
FIGS. 2 and 3 respectively are top and bottom plan views of the urinary catheter support of FIG. 1.

The sidewall 104 of the sheath portion 106 may have a proximal or rear edge 112. As illustrated in FIG. 2, in some embodiments, the rear edge 112 may be dipped, concave or rounded on a top side (FIG. 2) and bottom side (FIG. 3) thereof, for patient comfort.

Figure 8:
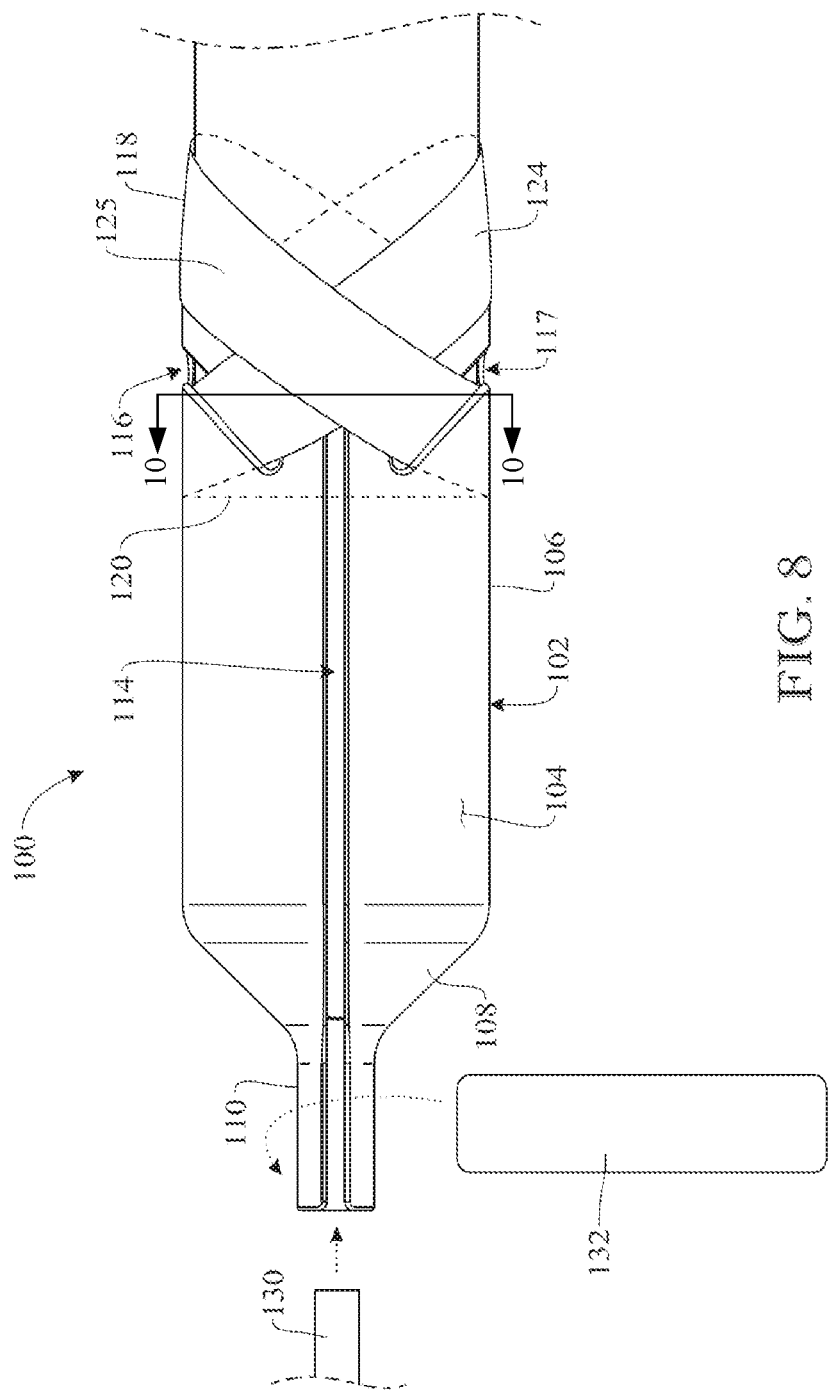
Figure 9:
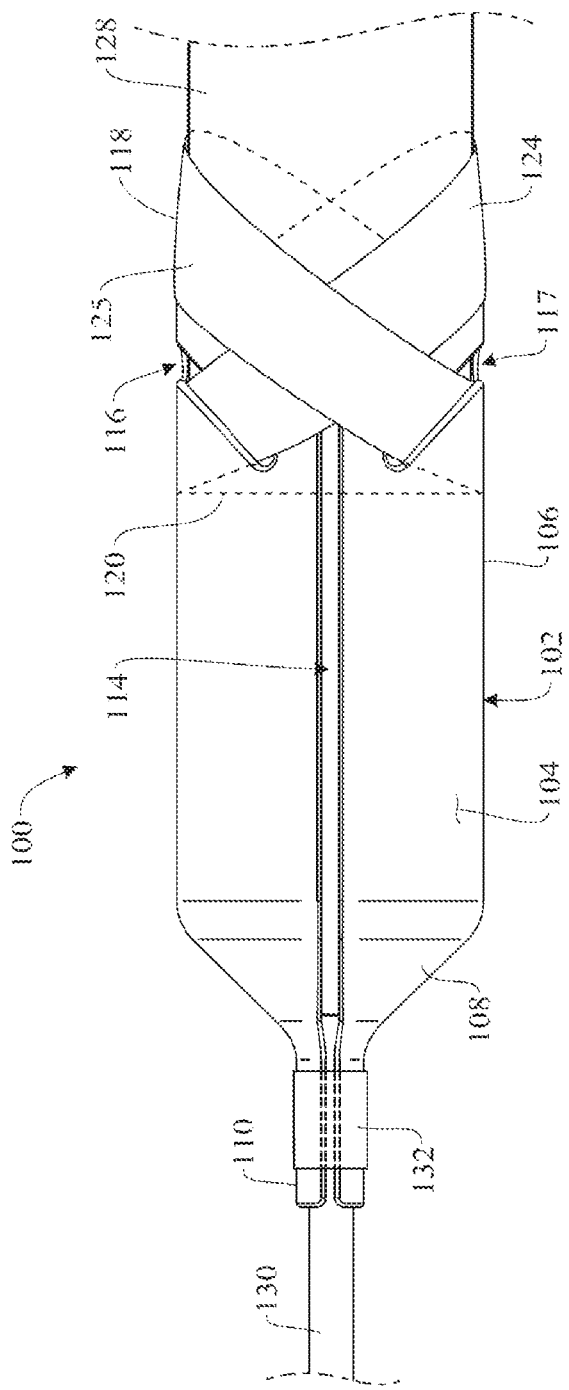

The main body 102 includes a front end 108 that extends from a front side of the main body 102 that is opposite the rear edge 112, and includes a catheter support 110 adjacent the longitudinal axis 101 for supporting an indwelling urinary catheter 130 (FIGS. 8 and 9). In some embodiments, the front end 108 includes one or more supporting members that extend toward the longitudinal axis 101 from the wider diameter sheath portion 106 to the catheter support 110. For example, the front end 108 may be tapered toward the longitudinal axis 101 as a substantially conical member, as shown in FIG. 1. The catheter support 110 may extend from the front end 108 along the axis 101 and provide a distal, narrow termination for supporting a catheter 130. In some embodiments, the front end 108 supports the catheter support 110 in substantially concentric alignment with the longitudinal axis 101 and the main body 102. Alternatively, the front end 108 may support the catheter support 110 at a location that is offset from the longitudinal axis 101.

The main body 102 and, optionally, the catheter support 110 and/or the front end 108 may be fabricated from any suitable material, such as a skin-compatible plastic material, for example. In some embodiments, the main body 102 is flexible. In some embodiments, the front end 108 and the catheter support 110 are relatively rigid compared to the main body 102. In some embodiments, the main body 102 may be fabricated of a lighter-weight material than the front end 108 and the catheter support 110, and/or the thickness of the material forming the main body 102 is less than that of the front end 108 and the catheter support 110. This more rigid front end 108 and catheter support 110 allows the front end 108 and the catheter support 110 to hold the urinary catheter 130 without yielding to pull and drag.

As mentioned above, the interior 105 of the sheath portion 106 is configured to receive the penis of a male patient. The sheath portion 106 may take on any suitable form and may completely surround the axis 101. In some embodiments, the main body 102 includes an elongated slot 114 that extends through the sidewall 104 of the sheath portion 106 and along the longitudinal axis 101 from the rear edge 112 toward the front end 108. In some embodiments, the slot 114 extends through the front end 108 and the catheter support 110. Accordingly, the main body 102, the front end 108, and/or the catheter support 110 may have a C-shaped design in a cross-section perpendicular to the longitudinal axis 101.

In some applications, the main body 102 may be deformed for opening the slot 114 to simplify receiving the penis 128 and a urinary catheter 130 (FIGS. 8 and 9) into the interior 105 of the urinary catheter support 100. The slot 114 may also have sufficient width to accommodate fluctuations in penile width. The front end 108 may have a sufficient length to accommodate fluctuations in penile length and reduce torsion in the urinary catheter 130. The catheter support 110 may have a sufficient length to reduce torsion in the urinary catheter 130.

The urinary catheter support 100 may take on any suitable dimensions for serving its purpose of supporting a urinary catheter 130 relative to a penis 128. In some non-limiting embodiments, the main body 102 may have a circumference of approximately 4-6 inches (±1 inch), and the slot 114 may have a width of approximately 0.1-1.0 inch, such as 0.25 inch. The main body 102 may have a length measured along longitudinal axis 101 of 3-5 inches, such as 4 inches. The catheter support 110 may have a diameter that is selected to accommodate various types of catheters, such as 0.5 inch, which can accommodate up to a 30 French catheter tube diameter. The front end 108 and the catheter support 110 may each have a length of 0.25-1.5 inches. It is understood that the above dimensions are exemplary dimensions for the components of the urinary catheter support 100, and that embodiments of the present disclosure cover variations of the support 100 having different dimensions.

The main body 102 may be secured to the penis 128 using any suitable technique. In some embodiments, the sheath portion diameter is formed sufficiently small to require an expansion or flexing of the sidewall 104 (i.e., widening of the slot 114) when the penis 128 is received in the interior 105 of the sheath portion 106. The sheath portion 106 may be formed sufficiently resilient that this flexing of the sidewall 104 causes the sheath portion 106 to squeeze or grab the penis 128, and facilitate removably securing the main body 102 to the penis.

In some embodiments, the main body 102 includes slits 116 and 117 that extend through the sidewall 104 of the sheath portion 106 for accommodating a strap 118 that is used to secure the urinary catheter support 100 to the penis 128. The slits 116 and 117 may be disposed at an oblique angle to the longitudinal axis 101 of the main body 102. In some embodiments, each slit 116, 117 may have a length of about 0.5-2.5 inches, such as 2.0 inches.

Figure 4:
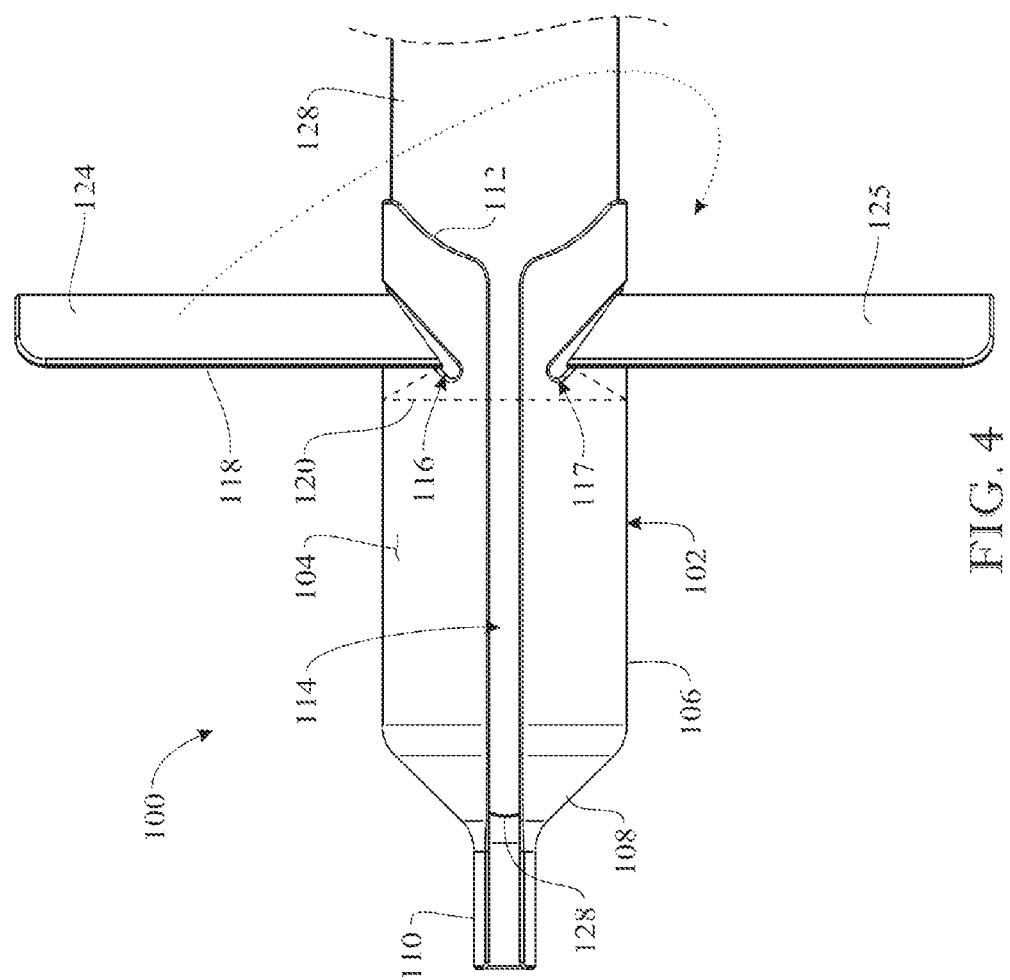
FIGS. 4-9 are top plan views illustrating steps of attaching the urinary catheter support of claim 1 on the penis of a male patient, in accordance with embodiments of the present disclosure.

In some embodiments, the strap 118 extends through the slits 116 and 117 and transverse to the longitudinal axis 101 within the interior 105 of the sheath portion 106. As illustrated in FIGS. 1 and 4, the strap 118 may include a middle strap segment 120, a first end strap segment 124, and a second end strap segment 125, wherein the first and second end strap segments 124 and 125 extend from opposite ends of the middle strap segment 120. The middle strap segment 120 extends inside the sheath interior 105 from the slit 116 to the slit 117. The end strap segments 124 and 125, in turn, protrude outwardly from the first and second slits 116 and 117, respectively, and are exterior to the main body interior 105. In some embodiments, the middle strap segment 120 may be curved and arranged along the inner side of the sidewall 104 of the sheath portion 106, as illustrated in FIG. 1. As discussed below in greater detail, the strap 118 extends between the penis 128 and the sidewall 104 when used to secure the urinary catheter support 100 to the penis 128.

The strap 118 may be formed of any suitable material. In some embodiments, the strap 118 includes a commercially-available elastic medical tape. The strap 118 may facilitate fastening of the urinary catheter support 100 by using both wrap and traction, yet stretching enough for fluctuations in penile width and length.

Figure 3:
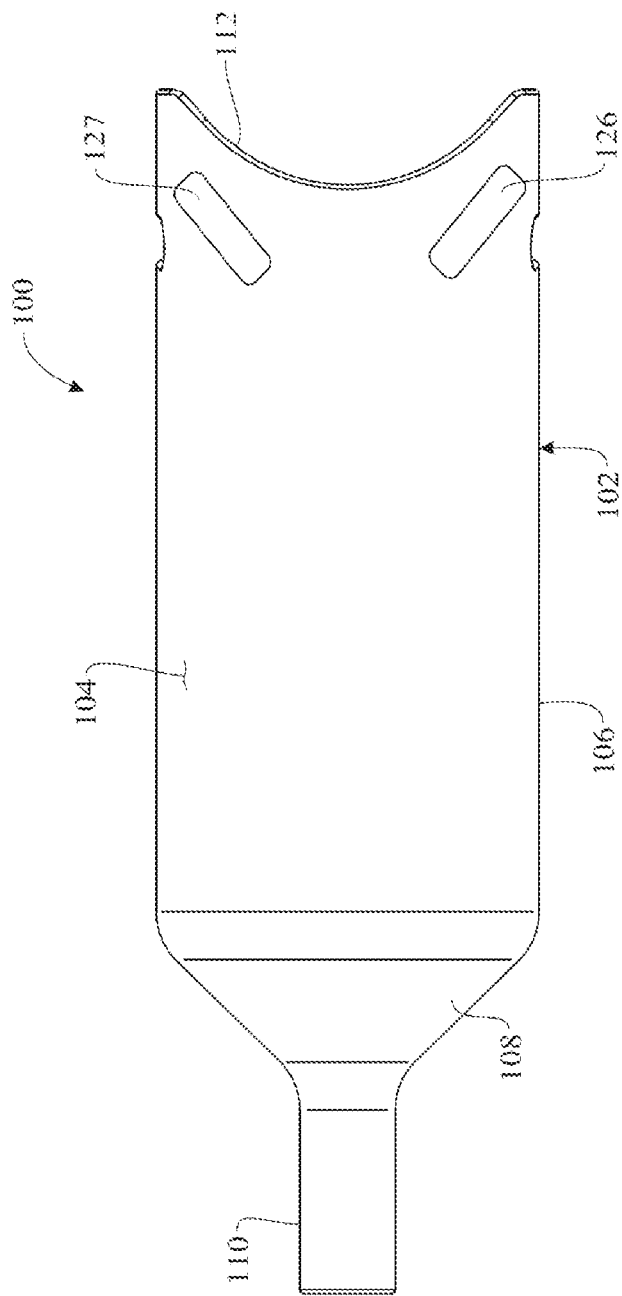
Figure 5:
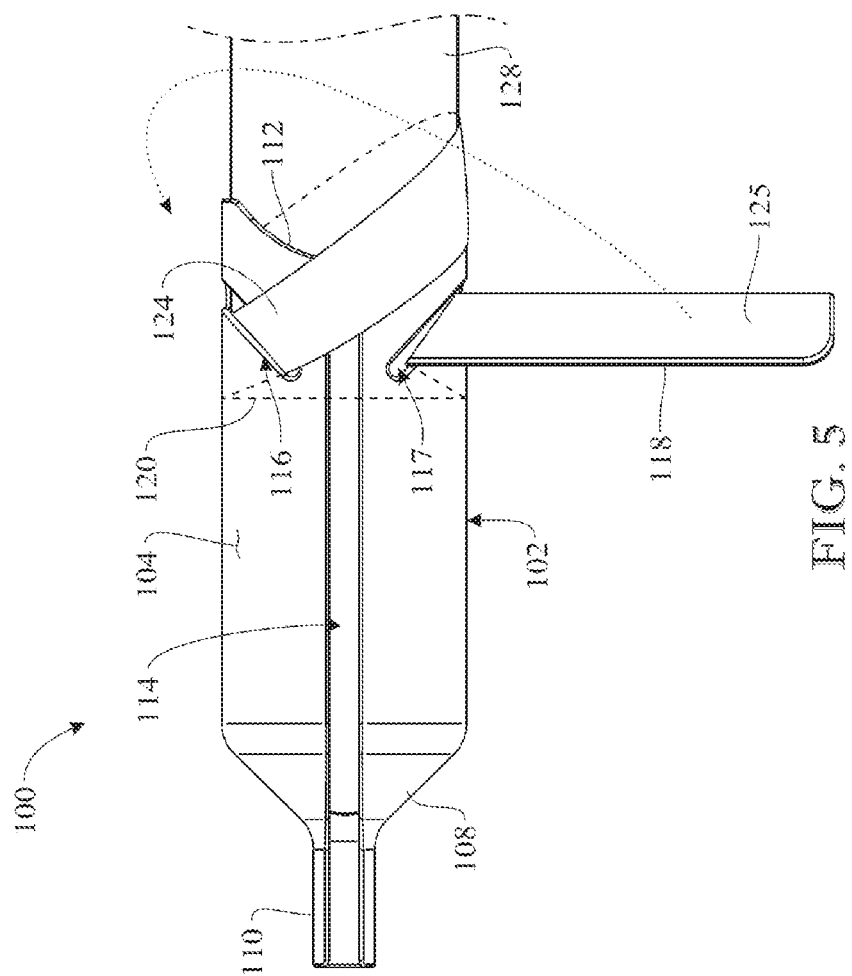
Figure 6:
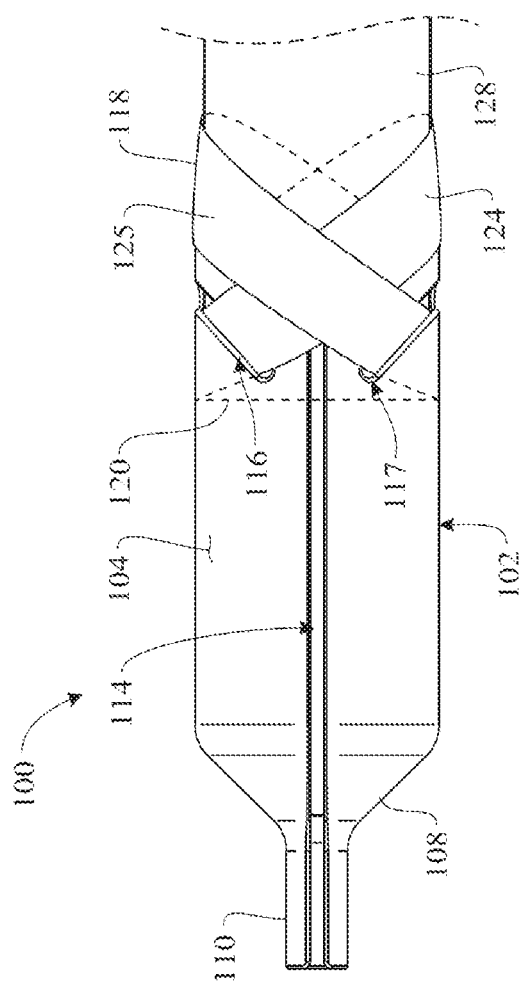

As illustrated in FIGS. 5 and 6, the first and second end strap segments 124 and 125 of the strap 118 may be suitably configured to detachably engage the sidewall 104 of the sheath portion 106 according to the knowledge of those skilled in the art. As illustrated in FIG. 3, in some embodiments, a pair of strap securing elements 126 may be provided on an exterior surface of the sidewall 104. The first and second end strap segments 124 and 125 of the strap 118 may be suitably configured to cross over each other to close the sheath slot 114 and detachably engage the respective strap securing elements 126. In some embodiments, the strap securing elements 126 may include hook-and-loop fasteners. In other embodiments, the strap securing elements 126 may additionally or alternatively include other devices or techniques which are capable of detachably engaging and securing the respective end strap segments 124 and 125 of the strap 118 to the main body 102.

Figure 10:
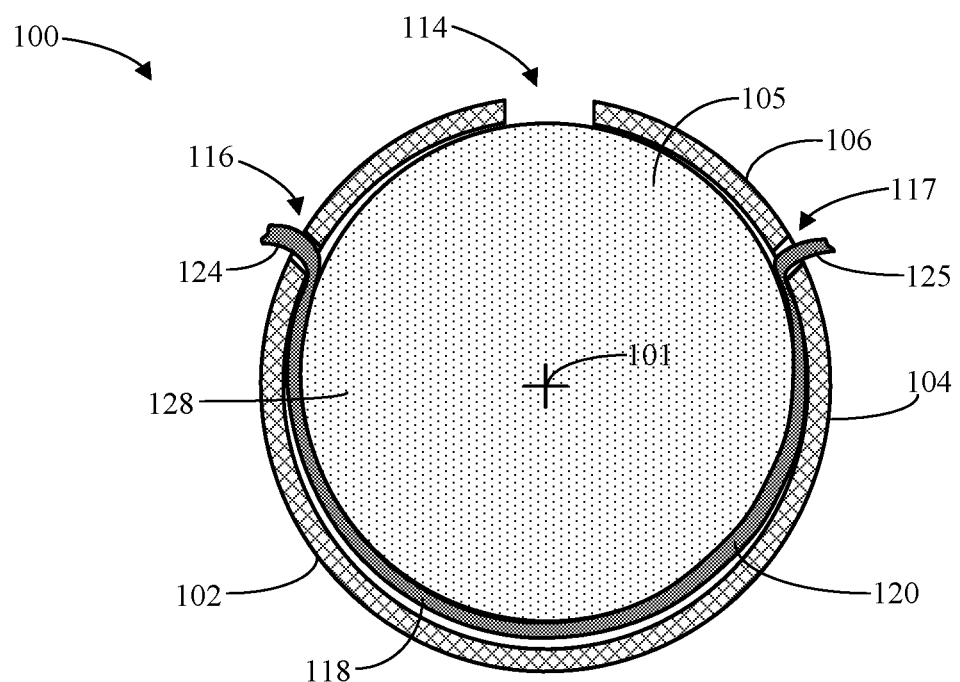
FIG. 10 is a cross-sectional view of the urinary catheter support of FIG. 8, taken generally along line 10-10.

As illustrated in FIGS. 4-9, in typical application, the urinary catheter support 100 may be deployed on the penis 128 of a male patient to secure a urinary catheter 130 (FIGS. 8 and 9) in place. Initially, as shown in FIG. 4, the flexible C-shaped main body 102 is opened by enlarging the slot 114, and the main body 102 is fitted onto the penis 128 of a male patient, with the penis 128 extending toward the front end 108 and the catheter support 110. The middle strap segment 120 of the strap 118 is positioned beneath the penis 128 and between the penis 128 and the sidewall 104 of the bottom side of the sheath portion 106, as shown in FIG. 10, which is a cross-sectional view of FIG. 8, taken generally along line 10-10. Thus, the penis 128 is positioned between the slot 114 and the middle strap segment 120.

Figure 7:
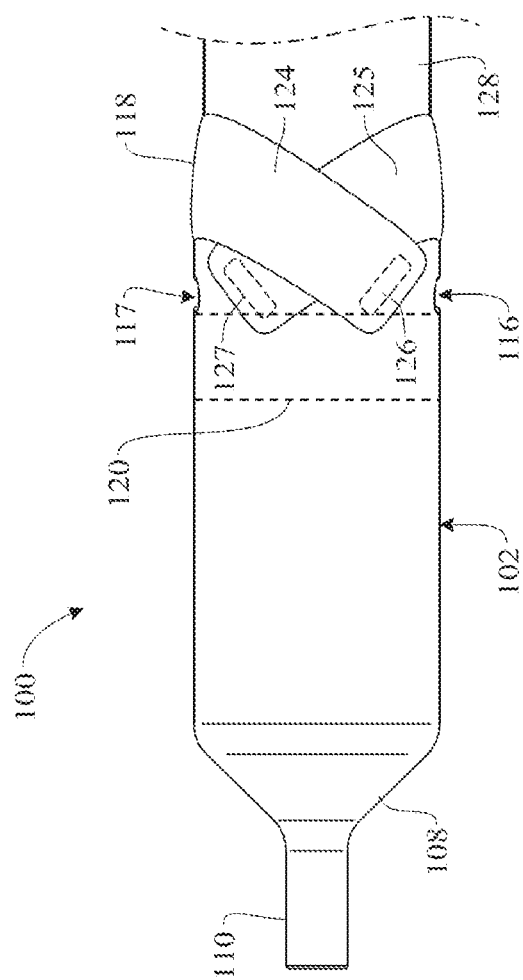

Next, as shown in FIGS. 4 and 5, the first end strap segment 124 of the strap 118 is pulled and extended from the first strap slit 116 towards the opposite side of the urinary catheter support 100, over and around the rear edge 112, towards the bottom side of the urinary catheter support (FIG. 7). As shown in FIGS. 6 and 7, the first end strap segment 124 is wrapped around the rear edge 112 and penis 128 to compress the sheath portion 106 of the main body 102 around and against the base of the penis 128, and is secured to the first strap securing element 126. Then, as shown in FIGS. 5 and 6, the second end strap segment 125 of the strap 118 is pulled and extended from the second strap slit 117 towards the opposite side of the urinary catheter support 100, over and around the rear edge 112, towards the bottom side of the urinary catheter support (FIG. 7). As shown in FIGS. 6 and 7, the second end strap segment 125 is wrapped around the rear edge 112 and penis 128 to compress the sheath portion 106 of the main body 102 around and against the base of the penis 128, and is secured to the second strap securing element 127.

In the attached position shown in FIGS. 6 and 7, the second end strap segment 125 extends across and over the first end strap segment 124 forming an X-type arrangement both on the top side (FIG. 6) and the bottom side (FIG. 7) of the urinary catheter support 100. In other words, the end strap segments 124, 125 of the strap 118 are crossed over each other and softly tightened to deform the sidewall 104 of the main body 102 and close the sheath slot 114, and detachably engage the respective strap securing elements 126, firmly yet comfortably securing the urinary catheter support 100 to the penis 128. The strap 118 assumes a concave shape as it is snugly stretched around the main body 102. The middle strap segment 120 of the strap 118 may accommodate and impart additional support and traction to the bottom side of the penis 128.

As illustrated in FIGS. 8 and 9, a urinary catheter 130 connected to a urine collection bag (not illustrated) may next be inserted first through the catheter support 110 and the front end 108 and then through the penis 128 and urethra (not illustrated) into the bladder of the patient. A neck closure strap 132 may be wrapped around the catheter support 110 to enclose the catheter support 110 in close tolerance around the urinary catheter 130 and then secured. The secured neck closure strap 132 and enclosing catheter support 110 prevent random transverse pull or movement of the urinary catheter 130 to support, center, and stabilize the urinary catheter 130 with respect to the catheter support 110 and the penis 128 and urethra, while allowing sliding movement of the urinary catheter 130 along the axis 101 relative to the catheter support 110, penis 128 and urethra, so as not to pull the bladder during various patient postures or fluctuating lengths of the penis 128.

In other applications, the urinary catheter support 100 may be deployed in place on a penis 128 in which the urinary catheter 130 is already installed. The catheter support 110 can be twisted or flexed to deform the main body 102 and widen the slot 114 for placement of the main body 102 on the penis 128 and the front end 108 and the catheter support 110 on the urinary catheter 130. Once the urinary catheter support 100 is placed on the penis 128 with the urinary catheter 130 inserted into the penis 128, the neck closure strap 132 may be applied to the catheter support 110 to enclose the catheter support 110 around the urinary catheter 130 which extends therethrough. Accordingly, the urinary catheter support 100 secures the urinary catheter 130 with respect to the penis 128 and urethra of the patient to prevent the "sawing effect" and consequent erosion of the penis 128 and urethra.

Further exemplary embodiments of the urinary catheter support 100 will be described with reference to FIGS. 11-15. These embodiments of the urinary catheter support 100 may include features described above with regard to FIGS. 1-10, which are identified by the same reference numbers.

Figure 11:
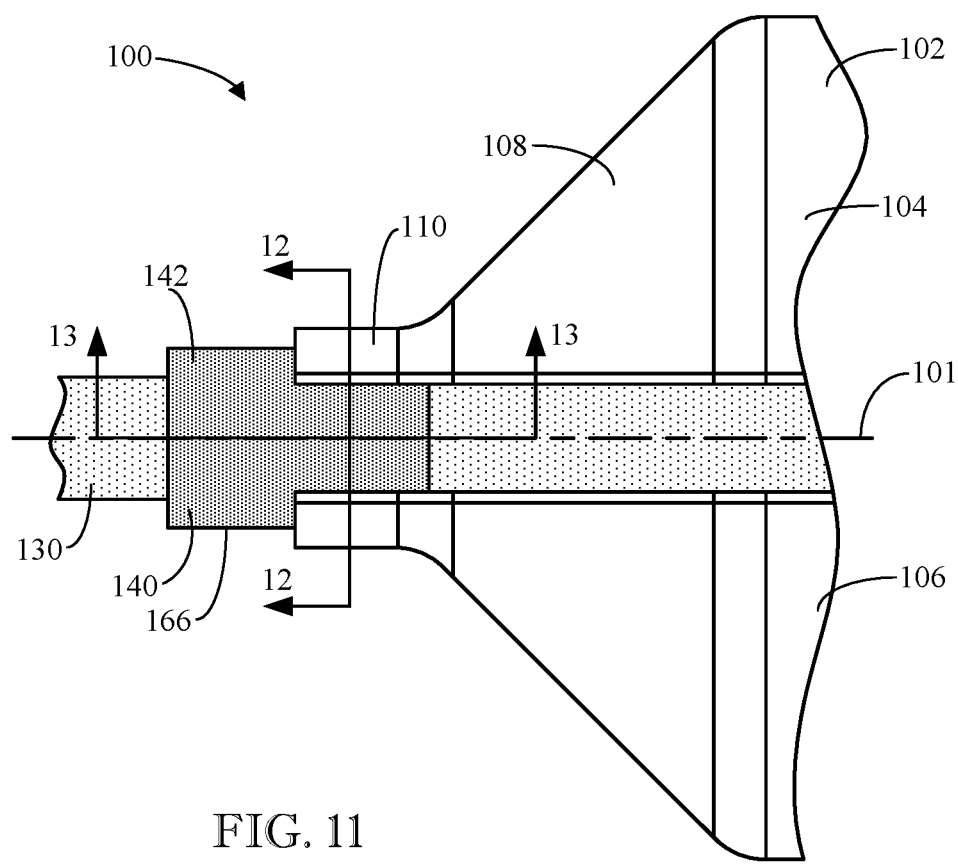
FIG. 11 is a simplified top view of a front end of a urinary catheter support in accordance with embodiments of the present disclosure.

In some embodiments, the urinary catheter support 100 includes a catheter collar or bushing 140, through which the catheter 130 extends, as shown in FIG. 11, which is a simplified top view of the front end 108 of the urinary catheter support 100 in accordance with embodiments of the present disclosure. The bushing 140 and the catheter 130 are shaded to more clearly illustrate the components in FIG. 11.

Figure 12:
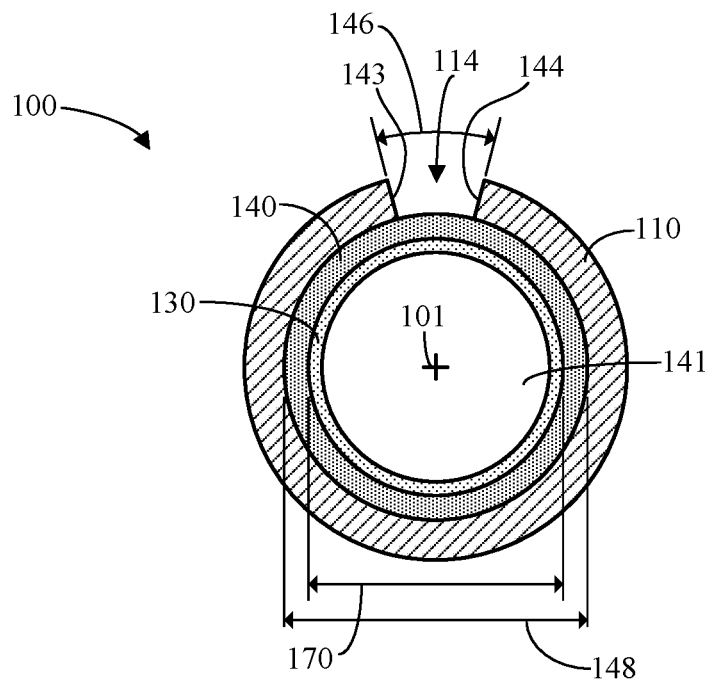
FIG. 12 is a front cross-sectional view of the urinary catheter support of FIG. 11 taken generally along line 12-12, in accordance with embodiments of the present disclosure.

The bushing 140 may be a cylindrical member formed of any suitable material, such as plastic or stainless steel, for example. In some embodiments, the bushing 140 includes a bore 141 through which the catheter 130 extends, as shown in FIG. 12, which is a cross-sectional view of FIG. 11 taken generally along line 12-12. The bushing 140 is held within the catheter support 110 to secure the catheter 130 to the support 110 of the main body 102 and the urinary catheter support 100. In some embodiments, the bushing 140 includes a distal end 142 that extends or protrudes distally from the catheter support 110, as shown in FIG. 11.

In some embodiments, the bushing 140 may be inserted into the catheter support 110 by sliding the bushing 140 along the longitudinal axis 101 into the catheter support 110. In some embodiments, the bushing 140 is configured to be snap-fit into the catheter support 110 through the slot 114. In some embodiments, the walls of the catheter support 110 are configured to flex to expand the slot 114 and allow the bushing 140 to pass through the expanded slot 114 into its received position illustrated in FIGS. 11 and 12.

In some embodiments, the slot 114 at the catheter support 110 is configured to facilitate this snap-fit reception of the bushing 140. For example, the slot 114 at the catheter support 110 may be defined by guide walls 143 and 144 that define an opening angle 146 relative to the axis 101. The angle 146 may be 20-40 degrees, such as 30 degrees. When the outer surface of the bushing 140 is pressed against the guide walls 143 and 144, the guide walls 143 and 144 drive the expansion of the slot 114 (i.e., expansion of the angle 146) and allow the bushing 140 to pass through the slot 114 and into its received position within the catheter support 110, which is shown in FIG. 12.

In some embodiments, the bushing 140 has an exterior diameter 148 that is slightly larger than the interior diameter of the catheter support 110. As a result, the bushing 140 is squeezed by the catheter support 110. Some embodiments of the bushing 140 are formed sufficiently rigid to prevent the collapse of the bushing 140 from the compressive forces applied to the bushing 140 by the catheter support 110. This prevents damage to a catheter 130 extending through the bushing 140 during snap-fit attachment of the bushing 140 to the catheter support 110.

Figure 13:
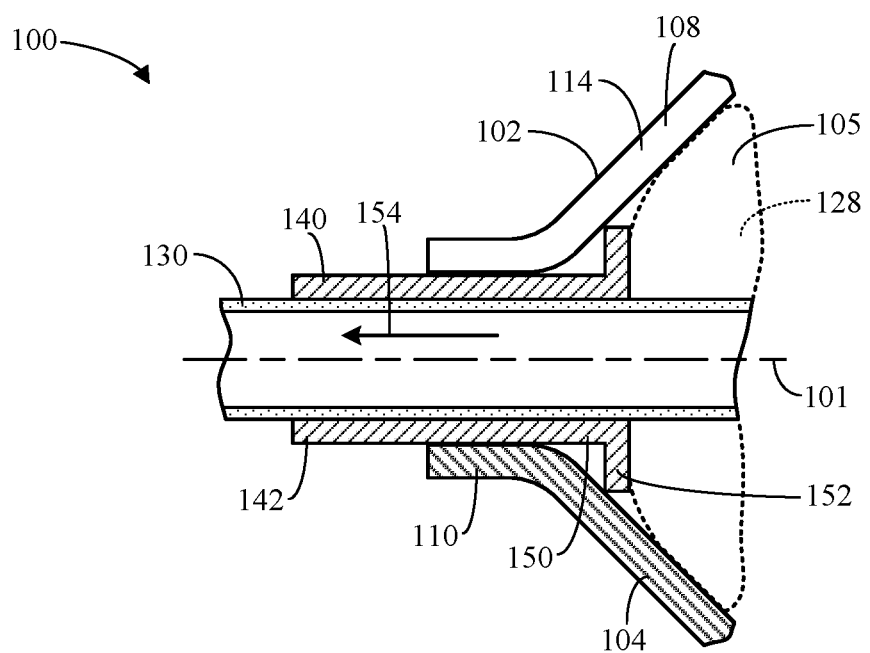
FIG. 13 is a side cross-sectional view of the urinary catheter support of FIG. 11 taken generally along line 13-13, in accordance with embodiments of the present disclosure.

Friction between the bushing 140 and the interior surface of the catheter support 110 resists sliding movement of the bushing 140 along the axis 101 relative to the catheter support 110. Some embodiments of the bushing 140 include features that further inhibit sliding movement of the bushing 140 along the axis 101 relative to the catheter support 110. In some embodiments, the bushing 140 includes a proximal end 150 that extends proximally from the catheter support 110 toward the interior 105 of the main body 102, as shown in FIG. 13, which is a side cross-sectional view of the urinary catheter support 100 of FIG. 11 taken generally along line 13-13, in accordance with embodiments of the present disclosure. In one embodiment, the bushing 140 includes a flange 152 at the proximal end 150, as shown in FIG. 13. The flange 152 extends obliquely to the axis 101, such as perpendicularly from the axis 101. The flange 152 prevents the bushing 140 from sliding in the direction 154 along the axis 101 relative to the catheter support 110 due to its engagement with the front end 108 of the main body 102. When the urinary catheter support 100 is installed on the penis 128 (phantom lines), the penis 128 prevents the bushing 140 from sliding along the axis 101 relative to the catheter support 110 in the direction that is opposite the direction 154. Thus, the flange 152 assists in maintaining the bushing 140 within the catheter support 110.

Figure 14:
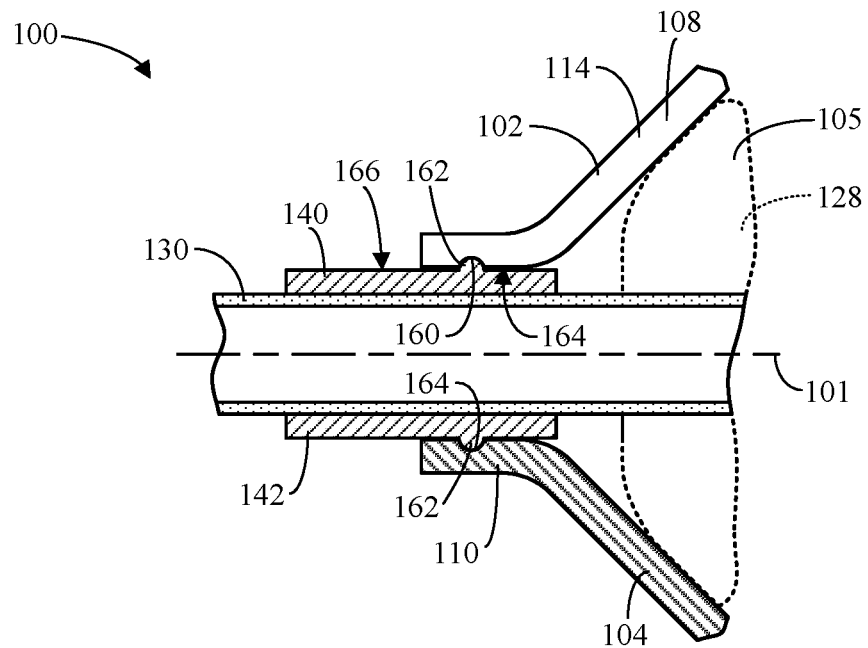
FIGS. 14 and 15 are side cross-sectional views of the urinary catheter support of FIG. 11 taken generally along line 13-13, in accordance with embodiments of the present disclosure.
Figure 15:
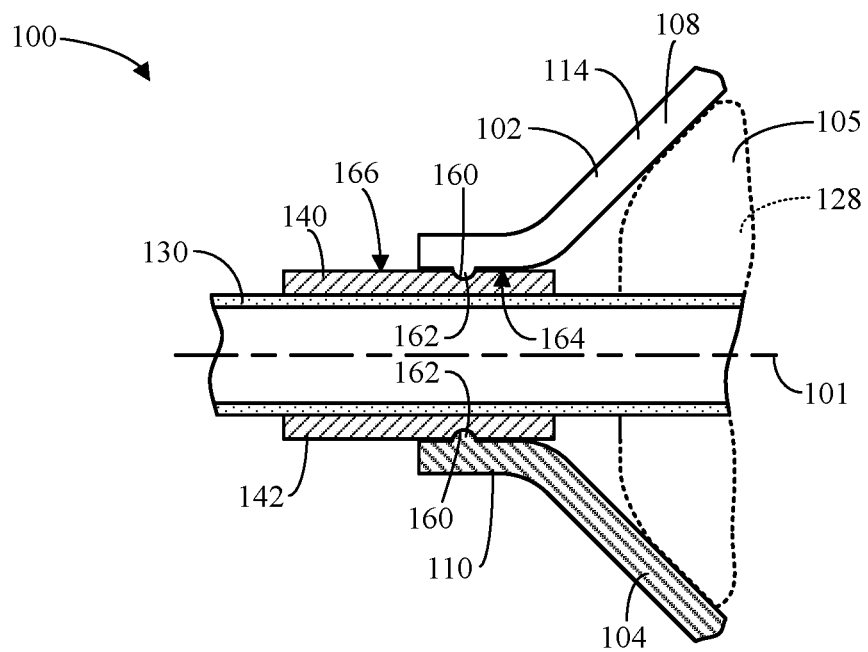

In some embodiments, the bushing 140 and the catheter support 110 include cooperating features that resist sliding movement of the bushing 140 relative to the catheter support 110 along the axis 101. In some embodiments, the bushing 140 and the catheter support 110 includes at least one detent 160 and at least one protrusion 162, as shown in FIGS. 14 and 15, which are side cross-sectional views of the urinary catheter support 100 of FIG. 11 taken generally along line 13-13, in accordance with embodiments of the present disclosure. The one or more protrusions 162 generally extend perpendicularly to the longitudinal axis 101 and are received within the corresponding detents 160, as shown in FIGS. 14 and 15. The reception of the one or more protrusions 162 within the detents 160 provides resistance to sliding movement of the bushing 140 along the axis 101 relative to the catheter support 110.

In some embodiments, the detents 160 are formed on an interior surface 164 of the catheter support 110, and the protrusions 162 extend from an exterior surface 166 of the bushing 140, as shown in FIG. 14. Alternatively, the detents 160 may be formed on the exterior surface 166 of the bushing 140, and the protrusions 162 may extend from the interior surface 164 of the catheter support 110, as shown in FIG. 15.

The one or more detents 160 may take on any suitable form. In some embodiments, the detents 160 may take the form of annular grooves that extend around the axis 101, such as in a plane that is substantially perpendicular to the axis 101. The detents 160 may also comprise groove segments that do not extend completely around the axis 101.

The one or more protrusions 162 may take on any suitable form. In some embodiments, the one or more protrusions 162 include an annular protrusion that extends around the axis 101, such as in a plane that is perpendicular to the axis 101. The one or more protrusions 162 may also include protrusion segments or nubs that do not extend completely around the axis 101.

The catheter 130 may be inserted through the bore 141 of the bushing 140 either before or after the bushing 140 is received within the catheter support 110. When the catheter 130 is inserted through the bushing 140 prior to installing the bushing 140 in the catheter support 110, the bushing 140 prevents the deformation of the catheter 130 during the snap-fit connection process due to the rigidity of the bushing 140, as mentioned above. Thus, in some embodiments, the bushing 140 substantially maintains its shape around the catheter 130 when the bushing 140 is pressed through the slot 114 of the catheter support 110 during installation of the bushing 140 in the catheter support 110. As a result, the bushing 140 can prevent damage to the catheter 130 during the snap-fit installation process.

As discussed above, it is desirable that the catheter 130 be allowed to slide relative to the catheter support 110 to facilitate insertion of the catheter 130 into the urethra of the penis 128, and to allow for movement of the catheter 130 relative to the urinary catheter support 100 during use by the patient after the catheter 130 has been inserted into the urethra of the patient. In some embodiments, the bore 141 of the bushing 140 has an interior diameter 170 that is slightly larger than the exterior diameter of the catheter 130 to allow the catheter 130 to slide relative to the bushing 140 along the axis 101.

The interior diameter 170 of the bushing 140 may be sized to accommodate a wide range of catheter diameters to allow a single bushing 140 to be used with different types of catheters 130. Alternatively, the interior diameter 170 of the bushing 140 may be sized to substantially conform to the outer diameter of specific catheters 130. As a result, the bushings 140 may be customized for specific catheters 130. Thus, one type of catheter 130 may require a bushing 140 having a smaller interior diameter 170 than a different catheter 130. In some embodiments, the bushing 140 is coded to identify its corresponding catheter 130, such as through a color coding system or an identification number matching system, for example.

Although the present invention has been described with reference to preferred embodiments, workers skilled in the art will recognize that changes may be made in form and detail without departing from the spirit and scope of the invention.

What is claimed is:

1. A urinary catheter support configured to support a catheter received in a penis of a male patient such that the catheter is secured relative to the penis, the urinary catheter support comprising:
    a flexible main body having an interior sized and configured to receive and accommodate the penis of a male patient;
    a catheter support at a front end of the main body configured to support a catheter adjacent a longitudinal axis of the main body;
    a slot extending along the longitudinal axis through the main body and the catheter support; and
    a strap including first and second end segments and a middle segment between the first and second end segments, wherein the first and second end segments respectively extend through first and second openings in the main body, and the middle segment extends through an interior of the main body.

2. The urinary catheter support of claim 1, wherein the front end tapers from the main body to the catheter support.

3. The urinary catheter support of claim 2, wherein the catheter support extends distally along the longitudinal axis from the front end of the main body.

4. The urinary catheter support of claim 1, further comprising a bushing received within the catheter support, the bushing including a bore through which the catheter extends.

5. The urinary catheter support of claim 4, wherein the bore has a diameter that is larger than an exterior diameter of the catheter.

6. The urinary catheter support of claim 5, wherein the catheter support squeezes the bushing in a radial direction relative to the longitudinal axis.

7. The urinary catheter support of claim 4, wherein a proximal end of the bushing includes a flange extending obliquely to the longitudinal axis.

8. The urinary catheter support of claim 4, wherein an interior surface of the catheter support and an exterior surface of the bushing include at least one cooperating detent and at least one protrusion, wherein that at least one protrusion and the at least one detent extend perpendicularly to the longitudinal axis, and the at least one protrusion is received within the at least one detent.

9. The urinary catheter support of claim 1, wherein the first and second openings in the flexible main body are each surrounded by a wall of the flexible main body.

10. The urinary catheter support of claim 9, wherein the first and second openings are formed on opposing sides of the slot.

11. The urinary catheter support of claim 10, wherein:
    the main body includes a rear edge that is opposite the front end; and
    the first and second openings are located closer to the rear edge than the front end.

12. A urinary catheter support comprising:
    a flexible main body having an interior sized and configured to receive and accommodate the penis of a male patient;
    a catheter support at a front end of the main body configured to support a urinary catheter adjacent a longitudinal axis of the main body;
    a slot extending along the longitudinal axis through the main body and the catheter support; and
    a bushing received within the catheter support, the bushing including a bore through which the urinary catheter extends,
    wherein:
        the catheter support squeezes the bushing in a radial direction relative to the longitudinal axis; and
        the bore has a diameter that is larger than an exterior diameter of the urinary catheter.

13. The urinary catheter support of claim 12, wherein the bushing extends distally from the catheter support along the longitudinal axis and away from the flexible main body.

14. The urinary catheter support of claim 12, wherein:
    the bushing extends proximally from the catheter support along the longitudinal axis and toward the interior of the main body; and
    a proximal end of the bushing includes a flange extending obliquely to the longitudinal axis.

15. The urinary catheter support of claim 12, wherein an interior surface of the catheter support and an exterior surface of the bushing include at least one detent and at least one protrusion, wherein that at least one protrusion and the at least one detent extend perpendicularly to the longitudinal axis, and the at least one protrusion is received within the at least one detent.

16. The urinary catheter support of claim 12, further comprising a strap including first and second end segments and a middle segment connecting the first and second end segments, wherein the first and second end segments respectively extend through first and second openings in the main body, and the middle segment extends through an interior of the main body.

17. A method of supporting a urinary catheter received in a penis of a male patient comprising:
   attaching a urinary catheter support to the penis including receiving the penis within an interior of a flexible main body; and
   installing a bushing within a catheter support at a front end of the main body, wherein the urinary catheter extends through a bore of the bushing, and the urinary catheter support squeezes the bushing in a radial direction relative to a longitudinal axis of the urinary catheter.

18. The method of claim 17, wherein attaching the urinary catheter support to the penis comprises:
   extending a strap through a first opening in the main body, between the penis and a sidewall of the main body, and through a second opening in the main body; and
   wrapping the strap around the penis and the main body, wherein the first and second openings in the flexible main body are each surrounded by a wall of the flexible main body.

19. The method of claim 17, further comprising restricting sliding movement of the bushing along the longitudinal axis relative to the urinary catheter support using at least one of:
   a flange extending from a proximal end of the bushing;
   a detent formed in an interior surface of the urinary catheter support and a protrusion formed on an exterior surface of the bushing; and
   a protrusion formed on the interior surface of the urinary catheter support and a detent formed on the exterior surface of the bushing.

20. The method of claim 17, wherein:
   the urinary catheter support squeezes the bushing in a radial direction relative to a longitudinal axis of the flexible main body; and
   the bore has a diameter that is larger than an exterior diameter of the urinary catheter.

* * * * *